(12) United States Patent
Clark (10) Patent No.: US 7,294,512 B2
(45) Date of Patent: Nov. 13, 2007

(54) SOLUTION FOR CALIBRATING A CHEMICAL ANALYZER FOR ALCOHOL, CARBONATE AND AMMONIA ASSAYS

(75) Inventor: Douglas Paul Clark, Newark, DE (US)

(73) Assignee: Dade Behring Inc., Deerfield, IL (US)

( * ) Notice: Subject to any disclaimer, the term of this patent is extended or adjusted under 35 U.S.C. 154(b) by 0 days.

(21) Appl. No.: 11/495,423

(22) Filed: Jul. 28, 2006

(65) Prior Publication Data

US 2006/0263885 A1 Nov. 23, 2006

Related U.S. Application Data

(63) Continuation of application No. 10/979,664, filed on Nov. 2, 2004, now abandoned.

(51) Int. Cl.
*G01N 21/93* (2006.01)
(52) U.S. Cl. .................... 436/8; 436/18; 436/113; 436/132; 436/133; 252/408.1
(58) Field of Classification Search .............. 436/8, 436/18, 113, 129, 131, 132, 133; 252/408.1
See application file for complete search history.

(56) References Cited

U.S. PATENT DOCUMENTS

| 3,824,237 | A | * | 7/1974 | Asako et al. ............... 540/230 |
|---|---|---|---|---|
| 3,960,497 | A | | 6/1976 | Accord |
| 4,278,636 | A | | 7/1981 | Voigt et al. |
| 4,678,754 | A | | 7/1987 | Hoskins |
| 4,843,013 | A | | 6/1989 | Chiang |
| 5,185,263 | A | | 2/1993 | Kroneis et al. |
| 5,238,845 | A | | 8/1993 | Tancredi et al. |
| 5,342,788 | A | | 8/1994 | Kunst et al. |
| 5,518,929 | A | | 5/1996 | Herring |
| 5,714,122 | A | | 2/1998 | Bretscher et al. |
| 5,795,789 | A | | 8/1998 | Dietzgen |
| 6,432,188 | B1 | | 8/2002 | Takai et al. |

* cited by examiner

*Primary Examiner*—Maureen M. Wallenhorst
(74) *Attorney, Agent, or Firm*—Leland K. Jordan (57) ABSTRACT

A multi-analyte calibration solution having known amounts of sodium carbonate, ammonium bicarbonate, and ethyl alcohol, with pH adjusted within a range between about 7.8 and 8.4.

8 Claims, 12 Drawing Sheets

SOLUTION FOR CALIBRATING A CHEMICAL ANALYZER FOR ALCOHOL, CARBONATE AND AMMONIA ASSAYS

This application is a Continuation of U.S. Ser. No. 10/979,664, filed Nov. 2, 2004, now abandoned.

BACKGROUND OF THE INVENTION

1. Field of the Invention

The present invention relates to standardized solutions containing stabilizers and analytes adjusted to specific levels for calibration of chemical analyzers. In particular, this invention relates to an aqueous based stabilized standard solution for the calibration of clinical assays for assessing blood alcohol levels, total carbon dioxide, and ammonia.

2. Description of the Related Art

Generally, automated biochemical analyzers employ a combination of analyte specific chemical reagents and reaction monitoring means to assay or determine the presence or concentration of a specific substance or analyte within a liquid sample suspected of containing that particular analyte. Such analyzers are well known and almost universally employ some sort of a calibration curve to determine analyte concentration from the signal generated by the reaction monitoring means in response to the presence of the analyte.

It is regular practice within the biochemical analytical industry to establish a full calibration curve for a chemical analyzer by using multiple calibration solutions or calibrators which have been carefully prepared with known, predetermined concentrations of analyte. These calibration or standard solutions are assayed one or more times and the mean resulting reaction signals are plotted versus their respective known analyte concentrations. A continuous calibration curve is then produced using any of several mathematical techniques chosen to produce an accurate replication of the relationship between a reaction signal and the analyte concentration. The shape of the calibration curve is affected by a complex interaction between reagents, analyte and the analyzer's electromechanical design. Thus, even if the theoretical analyte-reagent reaction is known, it is generally necessary to employ mathematical techniques to obtain an acceptable calibration curve. For greatest accuracy, calibration curves are established at regular intervals, to compensate for reagent particulars, and on individual analyzers, to compensate for equipment performance. The range of analyte concentrations used in establishing a full calibration curve is typically chosen to extend below and beyond the range of analyte concentrations expected to be found within biological samples like blood, serum, plasma, urine and the like.

Since analytical clinical procedures are typically designed to analyze serum samples, calibration solutions may be formulated using a matrix that is identical to or bioactively equivalent to serum. Human serum has typically been used as starting material for calibration solutions; however, the techniques used for stripping away interfering chemicals often produce process artifacts and wide lot-to-lot variations making it difficult to manufacture these solutions reproducibly. An additional disadvantage of calibration solutions containing human serum is that they cannot be stored for longer periods since serum contains many labile components which negatively affect the stability of the product. For this reason calibration materials are often provided in a dry state (lyophilized); however, inaccurate re-hydration of these materials commonly leads to inaccurate calibration measures. For these reasons, it is highly advantageous that calibration solutions be prepared using an aqueous or buffered solution as a base matrix.

U.S. Pat. No. 3,960,497 discloses the basic concepts of calibrating and verifying the calibration of a chemical analyzer using standard solutions having known values of the particular characteristic being measured.

U.S. Pat. No. 4,843,013 discloses a synthetic liquid control standard comprising an aqueous solution and several hemoglobin fractions, and sodium, potassium, lithium and calcium salts.

U.S. Pat. No. 5,342,788 discloses a serum-free standard solution containing TBG, albumin, and buffer. When T4 or T3 is added to this solution, an equilibrium is established between bound and free hormone resembling that observed in human serum. Stability of the synthetic standard solution is said to be superior to a solution based in human serum and furthermore, bovine TBG afforded superior stability than TBG derived from human serum.

U.S. Pat. No. 5,518,929 discloses aqueous solutions containing buffers and electrolytes adjusted for the calibration and quality control of both blood gases such as carbon dioxide and oxygen, using ion selective electrodes.

U.S. Pat. No. 5,795,789 discloses a stabilized standard solution for the calibration of clinical assays useful in assessing thyroid function, including total thyroxine, unbound thyroxine, total triiodothyronine, unbound triiodothyronine, and thyroid stimulating hormone.

In order to extend the amount of time that a liquid calibration solution may be accurately used to calibrate an analyzer, stabilizers and preservatives are added to the solution to extend the use-life of a calibrator by reducing degradation of the analyte and ensuring against contaminants. Consequently, the requirements placed on a formulation chemist to produce a combination of matrix, analyte, stabilizers and preservatives that are compatible with the analytical system, which can contain the desired concentrations of all desired analytes, and at the same time are able to maintain stability are found to be quite restrictive. These requirements are particularly challenging in the instance that one analyte in a multi-analyte calibration solution is basic and another analyte is acidic. In such an instance, those skilled in the art have been taught that the basic and acidic analytes would quickly react with one another to form water and a salt and thus a calibrator containing basic and acidic analytes would be expected to have a very short use-life. As a result of such a teaching, at least two different calibration solutions have previously been required to support calibration protocols for the acidic analytes alcohol and total carbon or carbonate and for the basic analyte ammonia. This imposes undesirable production expenses by the manufacturer as well as increased purchasing and handling expenses by the clinical laboratory.

Accordingly, there remains a need for a single calibration solution containing known amounts of alcohol, carbonate and ammonia analytes so as to increase flexibility in use as well as reduce all around expenses. However, it is traditionally expected in the art that the combination of basic and acidic analytes would inherently and adversely affect the stability of the calibration solution. Carbonates in particular are known to be readily decomposed by acids. Normally, basic solutions require a pH range greater than about pH=8 to be stable and acidic solutions a pH range lower than about pH=5 to be stable. Notwithstanding the teachings of the art, it is an object of the present invention to provide a single, stabilized calibration solution having known amounts of acidic alcohol, acidic carbonate and basic ammonia so that the advantages of having a multi-analyte calibration solution may be realized over an extended period of time.

SUMMARY OF THE INVENTION

The present invention is based upon the surprising discovery that a pH range can be established in a single liquid standard or calibration solution formulated simultaneously with specific amounts of blood alcohol (EtOH), total serum carbonate ($CO_2$), and blood ammonia ($NH_4$). Unexpectedly, the presence of basic and acidic analytes has been found to have no adverse effect on the utility of the calibration solution in measuring the analytes or on the stability of the solution as a whole. In addition, an extended period of usage or stability of the calibration solution may be achieved by including a combination of anti-microbial agents demonstrated to be active against gram-positive bacteria, gram-negative bacteria, spore-forming fungi, and non-spore-forming fungi without adversely affecting the utility of the calibration solution.

BRIEF DESCRIPTION OF THE DRAWINGS

The invention will be more fully understood from the following detailed description thereof taken in connection with the accompanying drawings which form a part of this application and in which.

DETAILED DESCRIPTION OF THE INVENTION

Important clinical assays include blood alcohol, carbonate and ammonia. Early social cultures learned that fermented fruits and grains produced a concoction containing ethanol or alcohol that produced a feeling of well being. In addition, ethanol-containing medicines have been used for treatment of multiple diseases. Excess consumption of alcohol however impairs those parts of the brain responsible for the most highly integrated body functions. Blood alcohol is usually measured for medico-legal reasons to determine if a person is intoxicated or in the diagnosis of coma in which alcohol may be the sole or contributing cause.

Measurement of total serum $CO_2$ is useful in determining the acid-base status of a patient. Total $CO_2$ concentration is greatly depressed in metabolic acidosis resulting from many different diseases, such as kidney failure, poisoning, diabetic ketoacidosis (DKA), and shock. Total $CO_2$ concentration is mildly increased in respiratory acidosis coming as a consequence of any lung disease that prevents removal of carbon dioxide. Common lung diseases that lead to respiratory acidosis include: chronic obstructive pulmonary disease, asthma, obesity hypoventilation syndrome, excessive fatigue of the diaphragm or muscles of the rib cage, or severe deformities of the spine and rib cage. Total carbon dioxide in serum or plasma exists as dissolved $CO_2$, carbamino derivatives of plasma protein and bicarbonate anion and these are generally acidified to covert all three forms to $CO_2$ gas for measurement.

Blood ammonia levels are used in pediatric patients for diagnosis of Reye's syndrome because blood ammonia is often elevated before liver enzymes and also in the diagnosis of certain inborn errors of metabolism. In adults, blood ammonia measurements are commonly used in management of hepatic coma and for monitoring nitrogen balance in patients being treated for hyper-alimentation.

As described herein and according to the present invention, a standard solution, or calibration solution, with extended stability and being capable of simultaneous use in methods for determination of blood alcohol (EtOH), total serum carbonate ($CO_2$), and blood ammonia ($NH_4$) is provided which can be produced in a simple manner from easily obtainable starting materials. The calibration solution according to the present invention contains only purified water as a base. A key feature of the present invention is enhancing and maintaining the buffering capacity of the calibration solution by establishing pH in a range between about 7.8 and 8.6 thereby providing a multi-analyte, stabilized calibration solution containing known amounts of acidic alcohol, acidic carbonate and basic ammonia.

Subsequent to addition of the alcohol, acidic carbonate and ammonia analytes, agents active against contaminating microbes may be included in the calibration solution to achieve a desired amount of stabilization. These agents may consist of any number of compounds which are effective against bacteria and fungi, are inert in the analytical system, and are unreactive towards components of the matrix of the calibration solution and the specific analytes contained therein. In an exemplary embodiment, Polymyxin B, an antibiotic isolated from strains of *Bacillus polymyxa*, is added at a concentration of about 0.02 g/L; sodium pyrithione (Omadine) may be optionally added at a concentration of 0.2-0.4 g/L. At these concentrations, Polymyxin B is active mainly against bacteria and sodium pyrithione is active primarily against fungi. It may also be found useful to add a broad spectrum anti-microbial agent to reinforce the activities of the others. As an example, 0.2 g/L of a 20% aqueous solution of polyhexamethylene biguanide (Cosmocil CQ) or 0.2 g/L of streptomycin may be added as protection against both gram-positive and gram-negative bacteria. A proprietary preservative known as ProClin 300 and available from Sigma-Aldridge has also been advantageously used. This particular group of agents has been found to be very effective in providing a sterile environment for the calibration solution of the present invention for an extended period of 400 days or more as discussed hereinafter. What is surprising is that the stability of the instant calibration solution has been found to be highly dependent upon the pH of the solution and nearly independent of the combination of preservatives used, some exemplary combinations being:

1. 0.4 g/L Omadine and 4 mg/L Polymoxin B and 20 mg/L Cosmocil CQ
2. 0.2 g/L Omadine and 0.2 g/L streptomycin
3. 0.2 g/L Omadine and 2 mg/L Polymoxin B
4. 0.5% Proclin 300

Subsequent to the preparation of the base aqueous matrix, the specific analytes of interest are added to produce a calibrator having the desired levels of analyte therein, depending upon the particulars of the analyzer being calibrated. Alcohol is preferably added in a range between 0-500 mg/dL, a range which covers the physiologically relevant concentrations found in human serum. Carbonate is preferably used in a range between 0 and 50 mmol/L solution since these concentrations span the physiologically relevant range of total carbon dioxide concentrations found in human serum. Ammonia is preferably used in a range between 0 and 1000 µmol/L solution since these concentrations span the physiologically relevant range of ammonia concentrations found in human serum.

Any combination of alcohol, carbonate and ammonia levels may be formulated in a calibration solution to achieve desired target values in a calibration solution, the only limitation being maintaining the pH level in a range between about 7.8 and 8.4.

Figure 1:
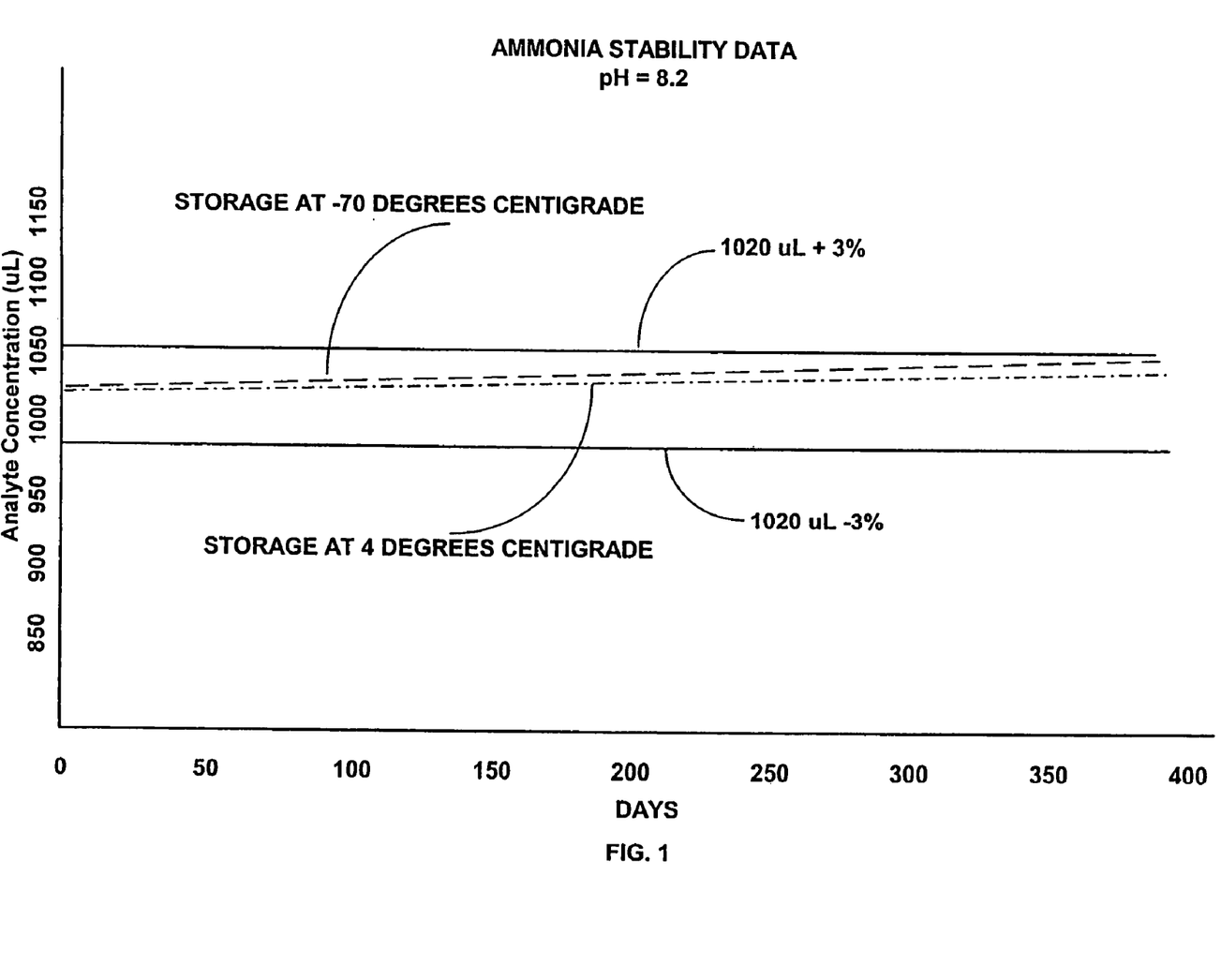
FIG. 1 is an illustration of ammonia stability in the alcohol, carbonate and ammonia multi-analyte calibrator of the present invention.
Figure 2:
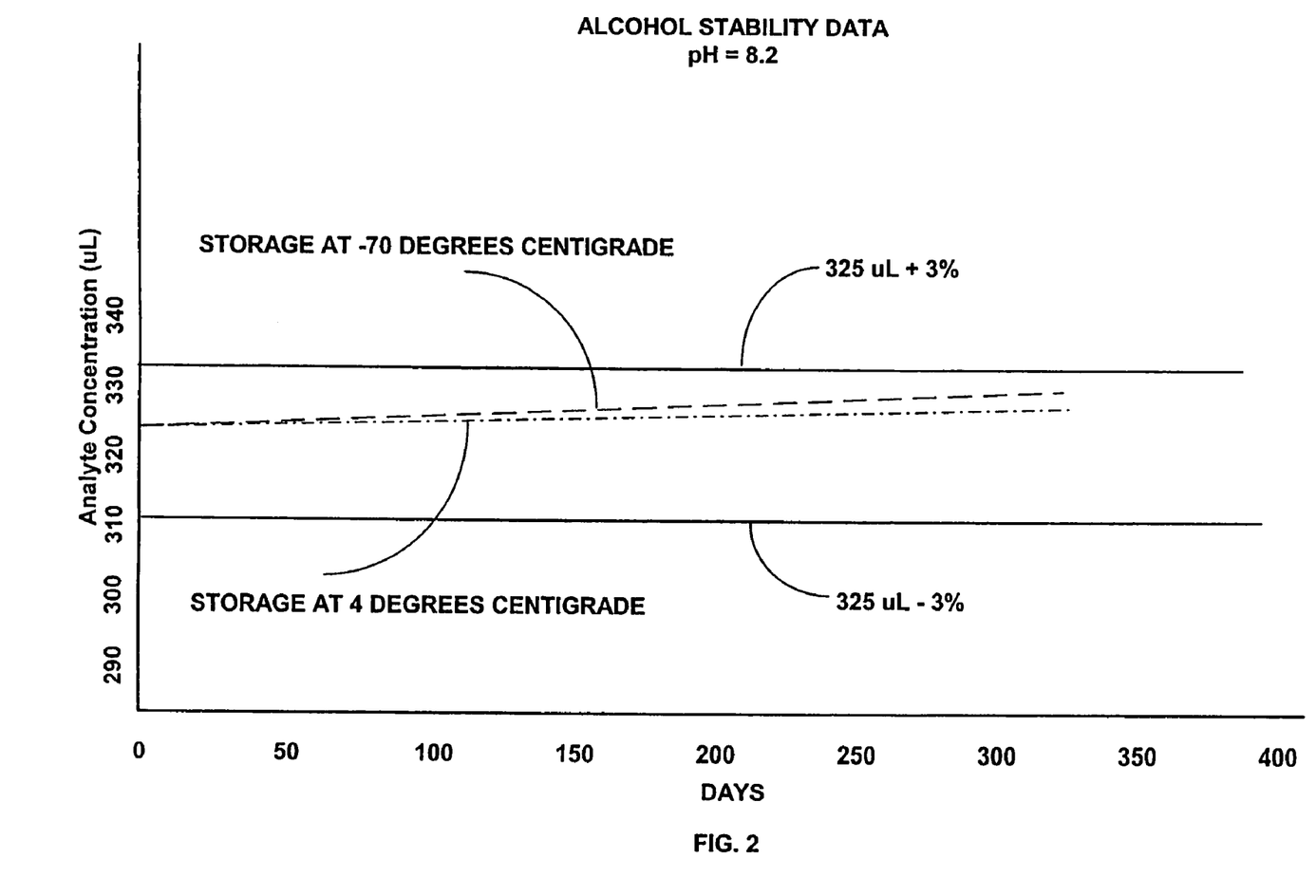
FIG. 2 is an illustration of alcohol stability in the alcohol, carbonate and ammonia multi-analyte calibrator of the present invention.
Figure 3:
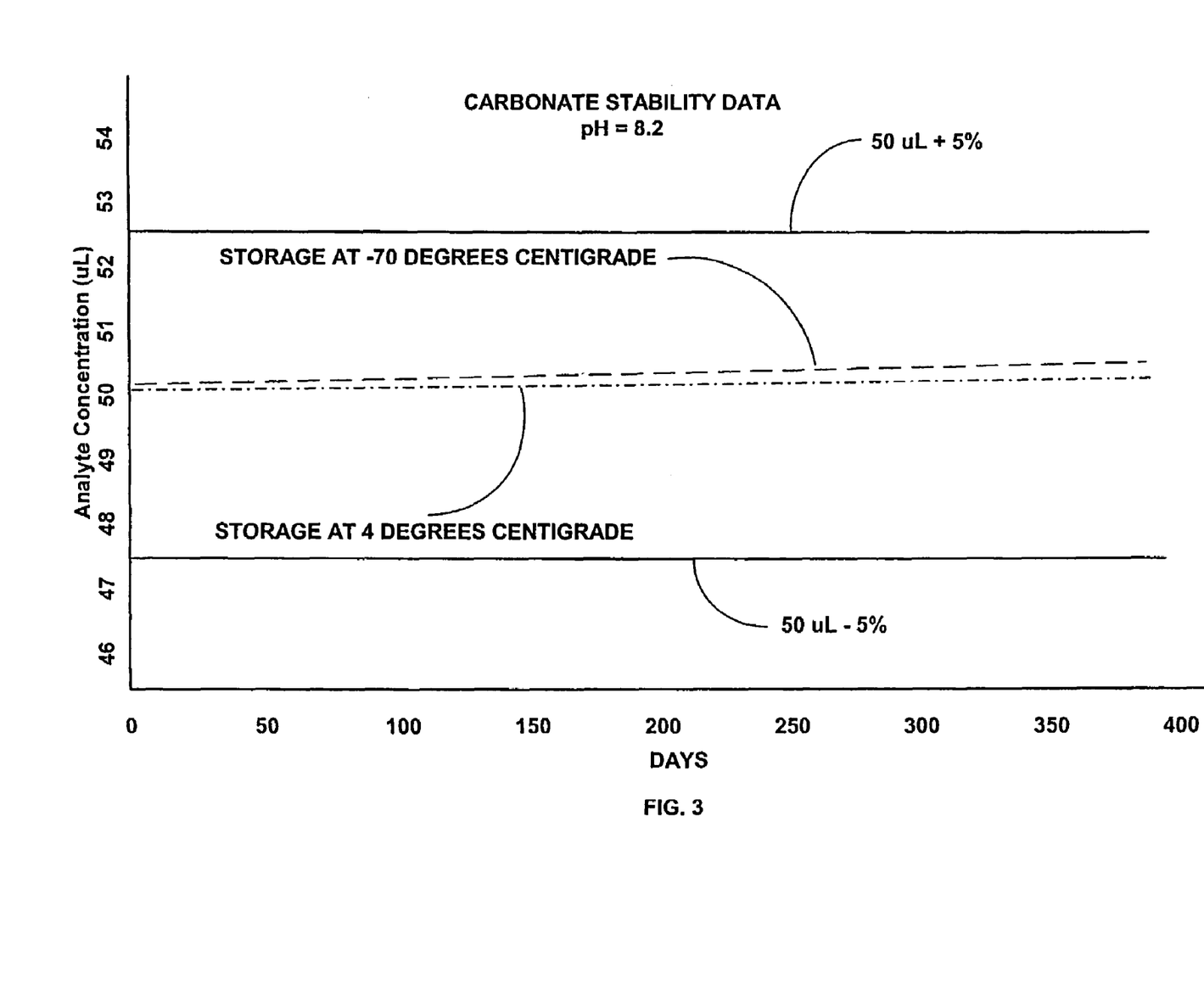
FIG. 3 is an illustration of carbonate stability in the alcohol, carbonate and ammonia multi-analyte calibrator of the present invention.

FIGS. 1-3 illustrate the analyte concentration stability as measured over a 400 day period for the alcohol, carbonate and ammonia multi-analyte calibrator of the present invention. FIG. 1 particularly illustrates ammonia stability as remaining within a ±3% range of a normal 1085 µmol/L ammonia value for two samples, stored in a closed container at both −70° C. and at +4° C. As described above, the pH of the multi-analyte calibrator was adjusted to 8.2.

Similarly, FIG. 2 particularly illustrates alcohol stability as remaining within a ±3% range of a normal 310 mg/dL alcohol value for the same two samples, stored in a closed container at both −70° C. and at +4° C. In accord with the present invention, the pH of the multi-analyte calibrator was adjusted to 8.2.

Finally, FIG. 3 particularly illustrates carbonate stability as remaining within a ±5% range of a normal 46.5 mmol/L carbonate value for the same two samples, stored in a closed container at both −70° C. and at +4° C. In accord with the present invention, the pH of the multi-analyte calibrator was adjusted to 8.2.

Figure 4:
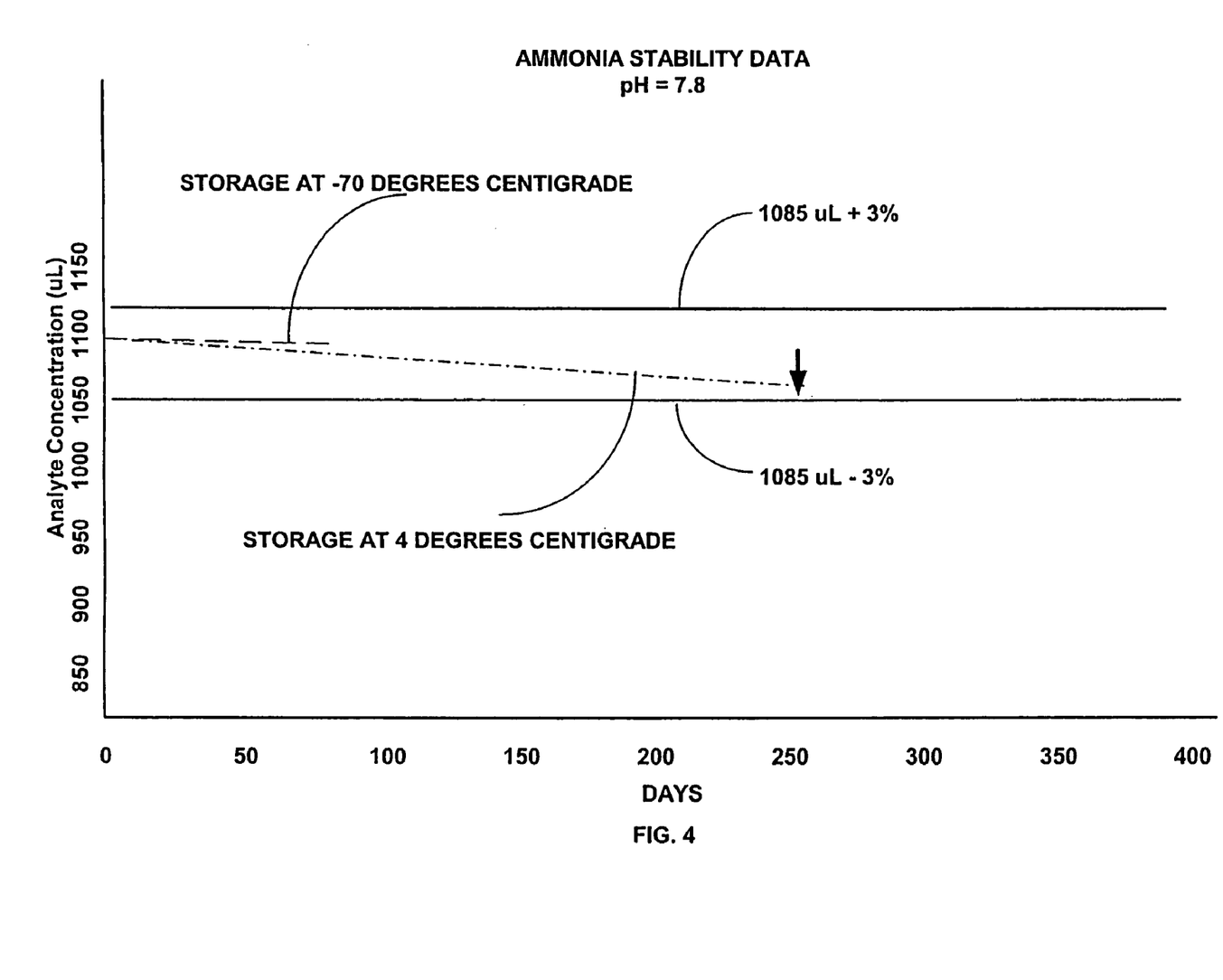
FIG. 4 is a first illustration of ammonia instability in an alcohol, carbonate and ammonia multi-analyte calibrator outside the acceptable pH range of the present invention.

In contrast, FIG. 4 illustrates the adverse effect on ammonia stability as a consequence of adjusting the pH of the alcohol, carbonate and ammonia multi-analyte calibrator of the present invention below 8.2 to 7.8. After about 250 days, as indicated by the downwards arrow, ammonia stability approaches the ±3% range of a normal 1085 µmol/L value for the sample stored under normal conditions at +4° C. Stability data for the sample stored under freezer conditions at −70° C. were not completed in view of data gathered at pH 7.4 described below.

Figure 5:
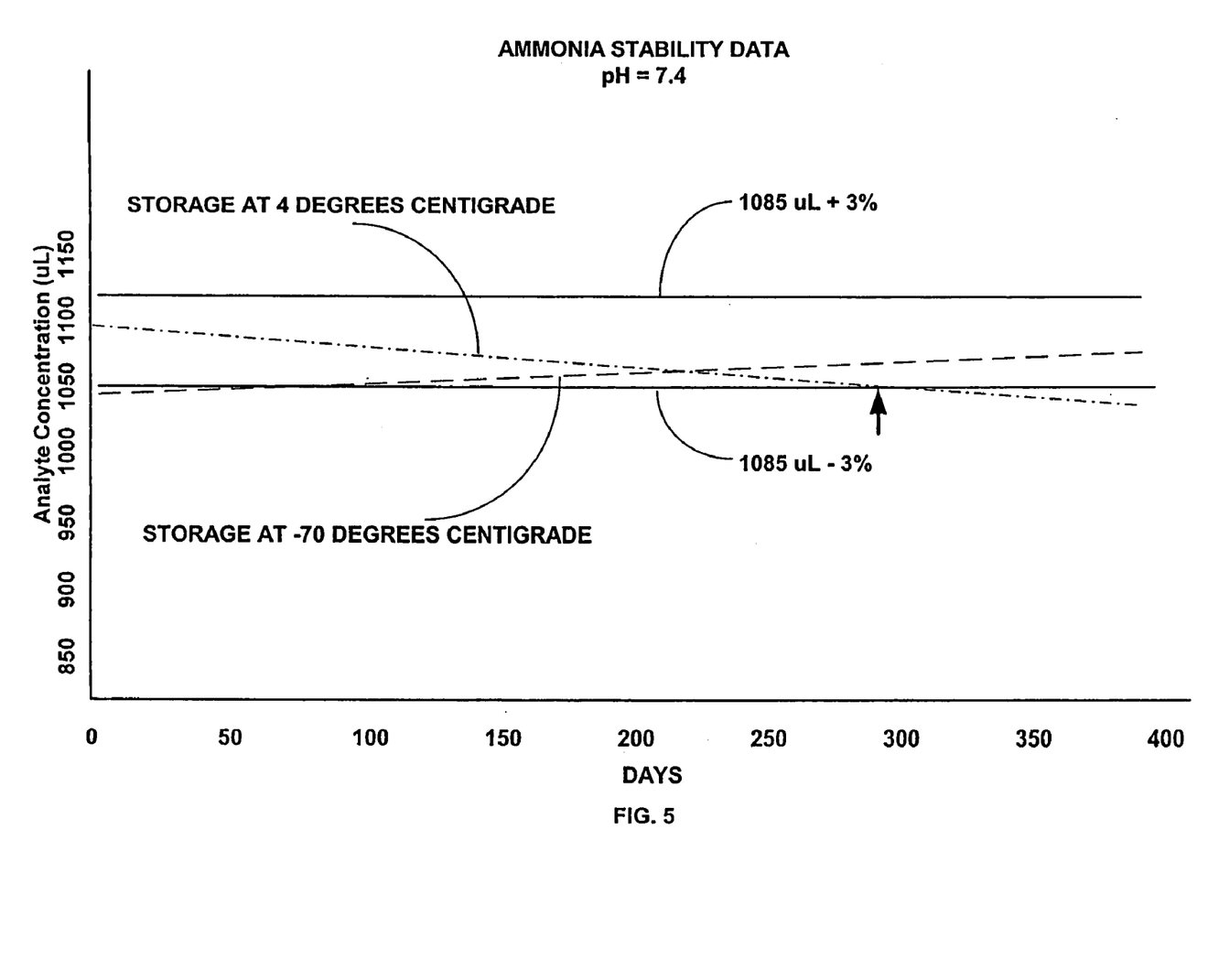
FIG. 5 is a second illustration of ammonia instability in an alcohol, carbonate and ammonia multi-analyte calibrator outside the acceptable pH range of the present invention.

FIG. 5 illustrates the adverse effect on ammonia stability as a consequence of further lowering the pH of the multi-analyte calibrator to 7.4. After about 300 days, as indicated by the upwards arrow, ammonia stability falls outside the ±3% range of a normal 1085 µmol/L value for the sample stored under normal conditions at +4° C.

Figure 6:
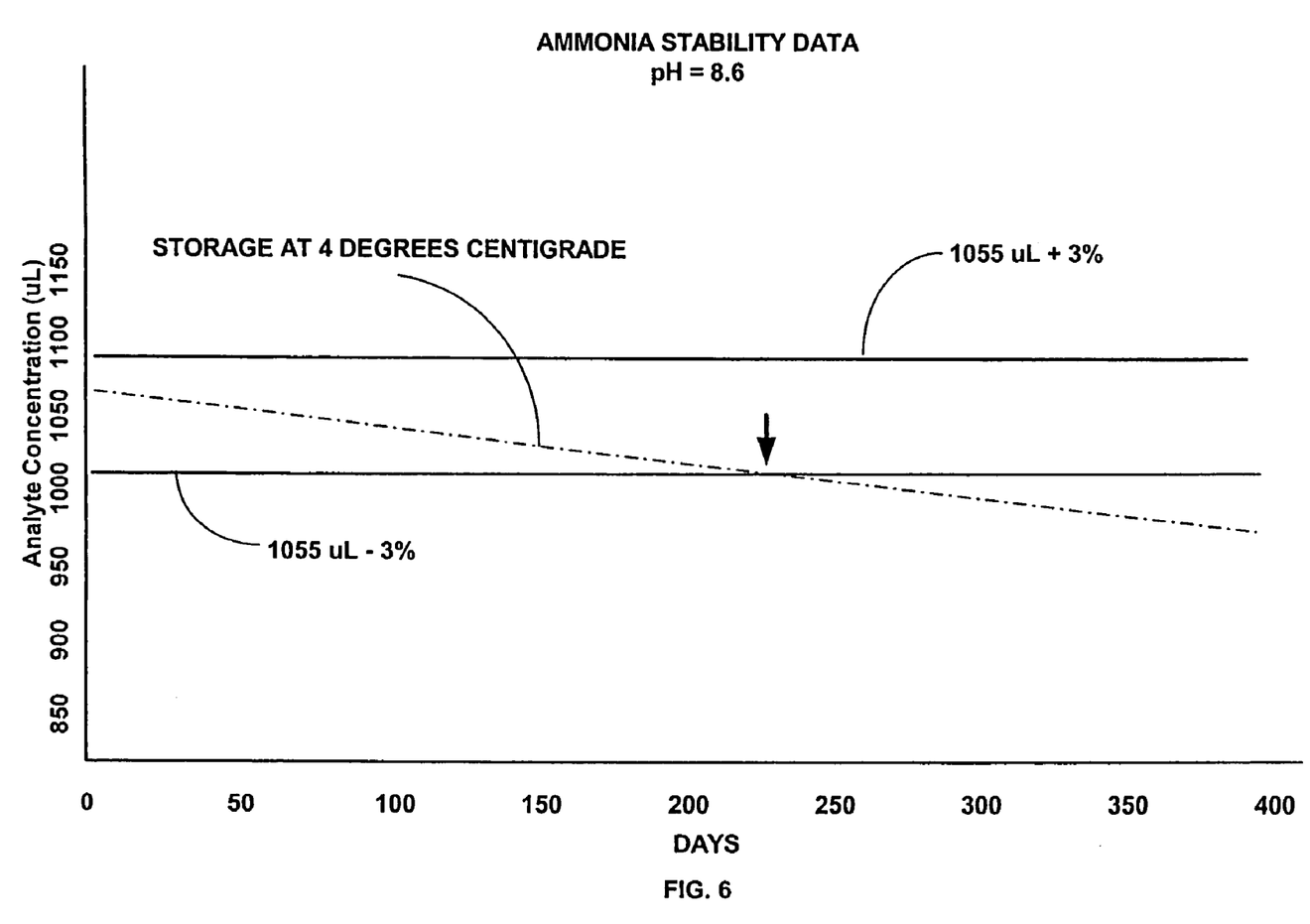
FIG. 6 is a third illustration of ammonia instability in an alcohol, carbonate and ammonia multi-analyte calibrator outside the acceptable pH range of the present invention.

Finally, FIG. 6 illustrates the adverse effect on ammonia stability as a consequence of raising the pH of the multi-analyte calibrator above 8.2 to 8.6. After 225 days, as indicated by the upwards arrow, ammonia stability falls outside the ±3% range of a normal 1085 µmol/L value the sample stored under normal conditions at +4° C. The combination of FIGS. 1-6 show that a alcohol, carbonate and ammonia multi-analyte calibrator having pH adjusted to a range between 7.8 and 8.6, centered at 8.2, as taught by the present invention, remains within acceptable stability conditions when stored at normal +4° C. in a closed container. In order to emphasize this dependence of stability upon the pH of the solution and as not affected by any preservatives in the multi-analyte calibrator, accelerated, high temperature stability tests were conducted on a alcohol, carbonate and ammonia multi-analyte calibrator having pH adjusted to a range between 7.8 and 8.6, centered at 8.2, as taught by the present invention with preservatives, illustrated in FIGS. 7-8-9. These FIGS. 7-8-9 may be compared with FIGS. 7A-8A-9A, respectively, for the same alcohol, carbonate and ammonia multi-analyte calibrator but not having any preservatives included.

Figure 7:
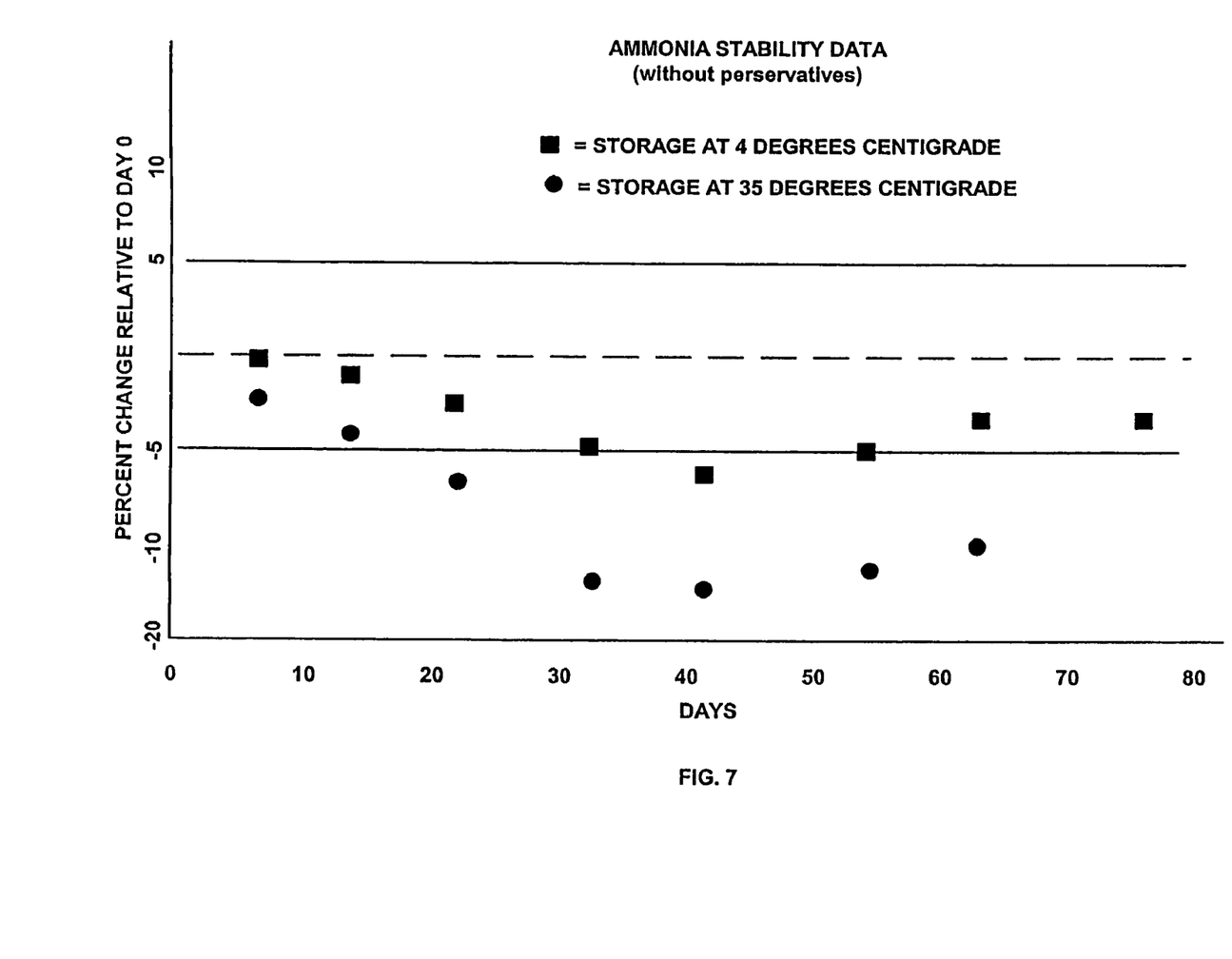
FIG. 7 is an illustration of alcohol stability in an alcohol, carbonate and ammonia multi-analyte calibrator of the present invention with preservatives therein.
Figure 7A:
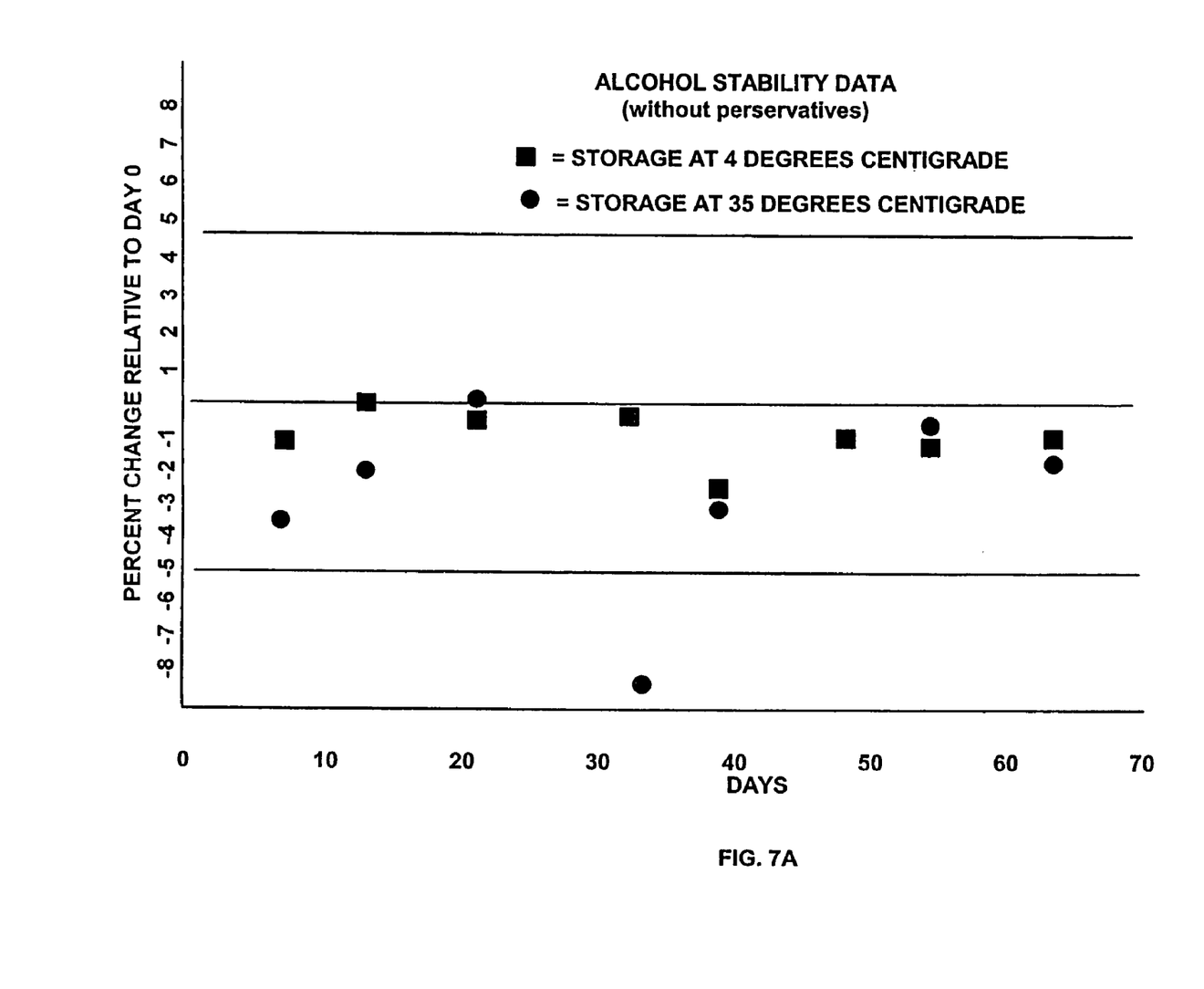
FIG. 7A is an illustration of alcohol stability in an alcohol, carbonate and ammonia multi-analyte calibrator of the present invention without preservatives therein.

FIGS. 7 and 7A illustrate alcohol stability as remaining within a ±5% range of a normal 310 mg/dL alcohol value for samples with and without preservatives, stored at both +4° C. and at +35° C. The sets of data are essentially equivalent, with the exception of a probable outlier at about day 33 in FIG. 7A, indicating that the presence or absence of preservatives was not relevant.

Figure 8:
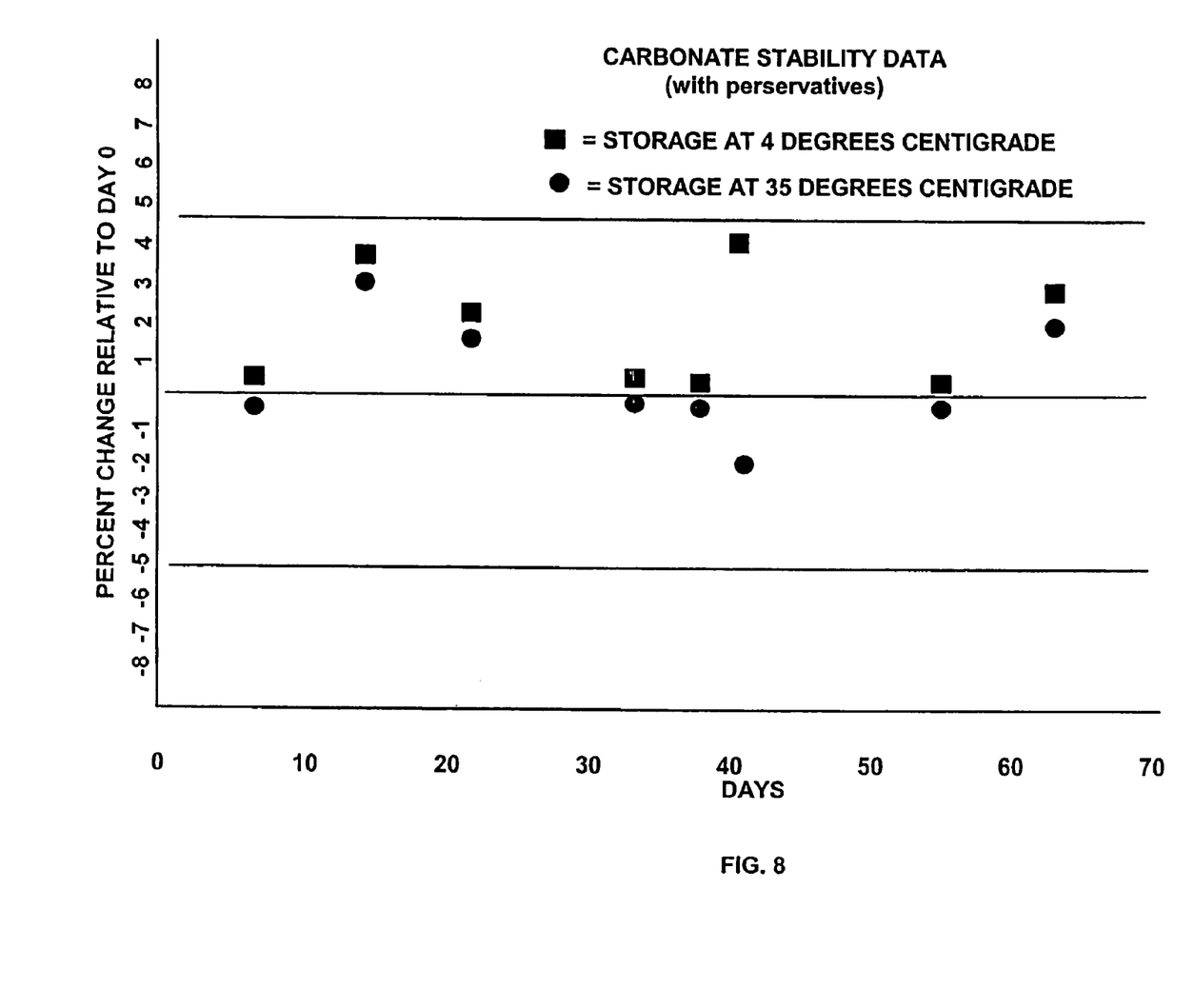
FIG. 8 is an illustration of carbonate stability in an alcohol, carbonate and ammonia multi-analyte calibrator of the present invention with preservatives therein.
Figure 8A:
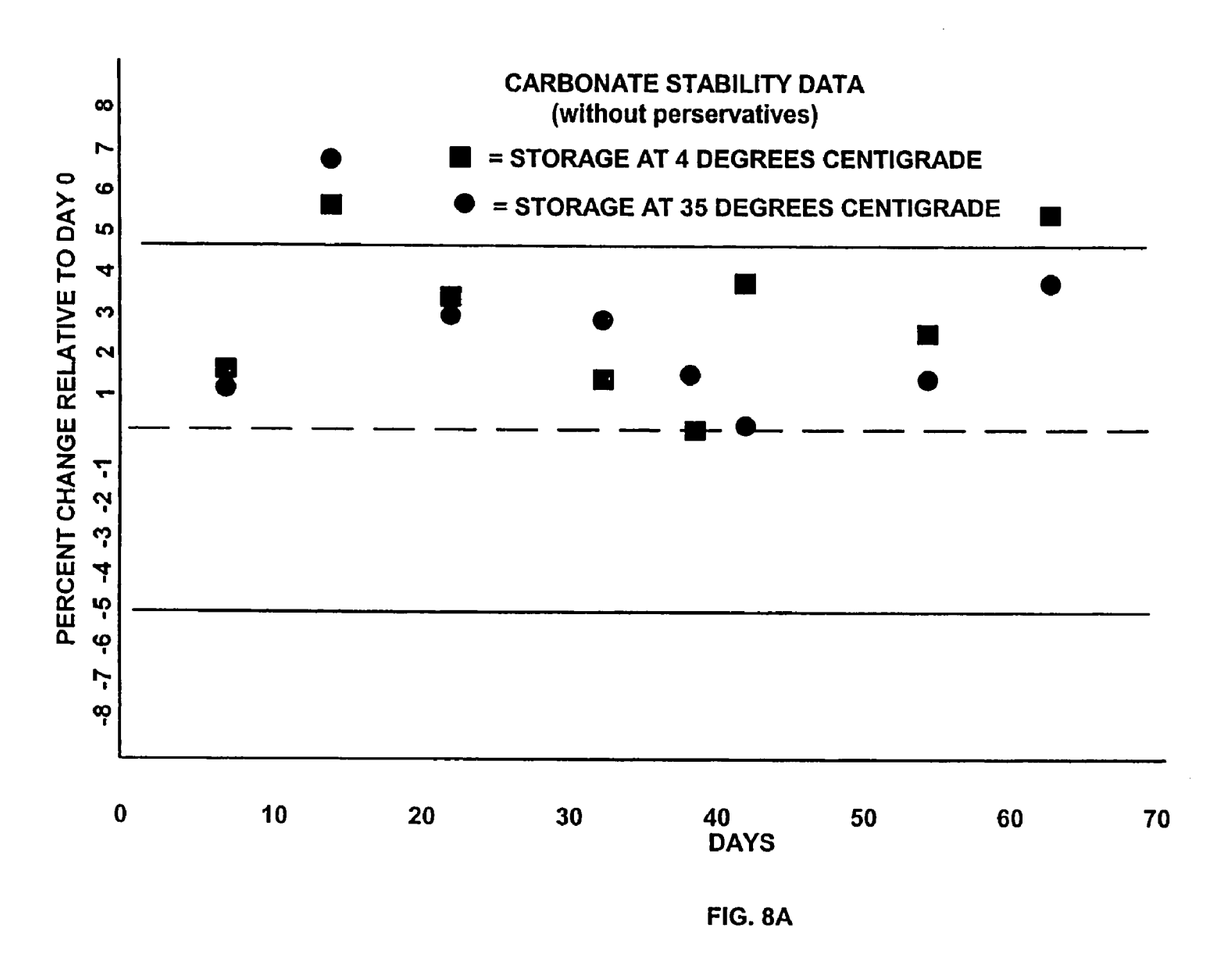
FIG. 8A is an illustration of carbonate stability in an alcohol, carbonate and ammonia multi-analyte calibrator of the present invention without preservatives therein.

Similarly, FIGS. 8 and 8A illustrate carbonate stability as remaining within a ±5% range of a normal 50 mmol/L carbonate value for samples with and without preservatives. Again, the sets of data are essentially equivalent, with the exception of a probable outlier at about day 15 in FIG. 8A.

Figure 9:
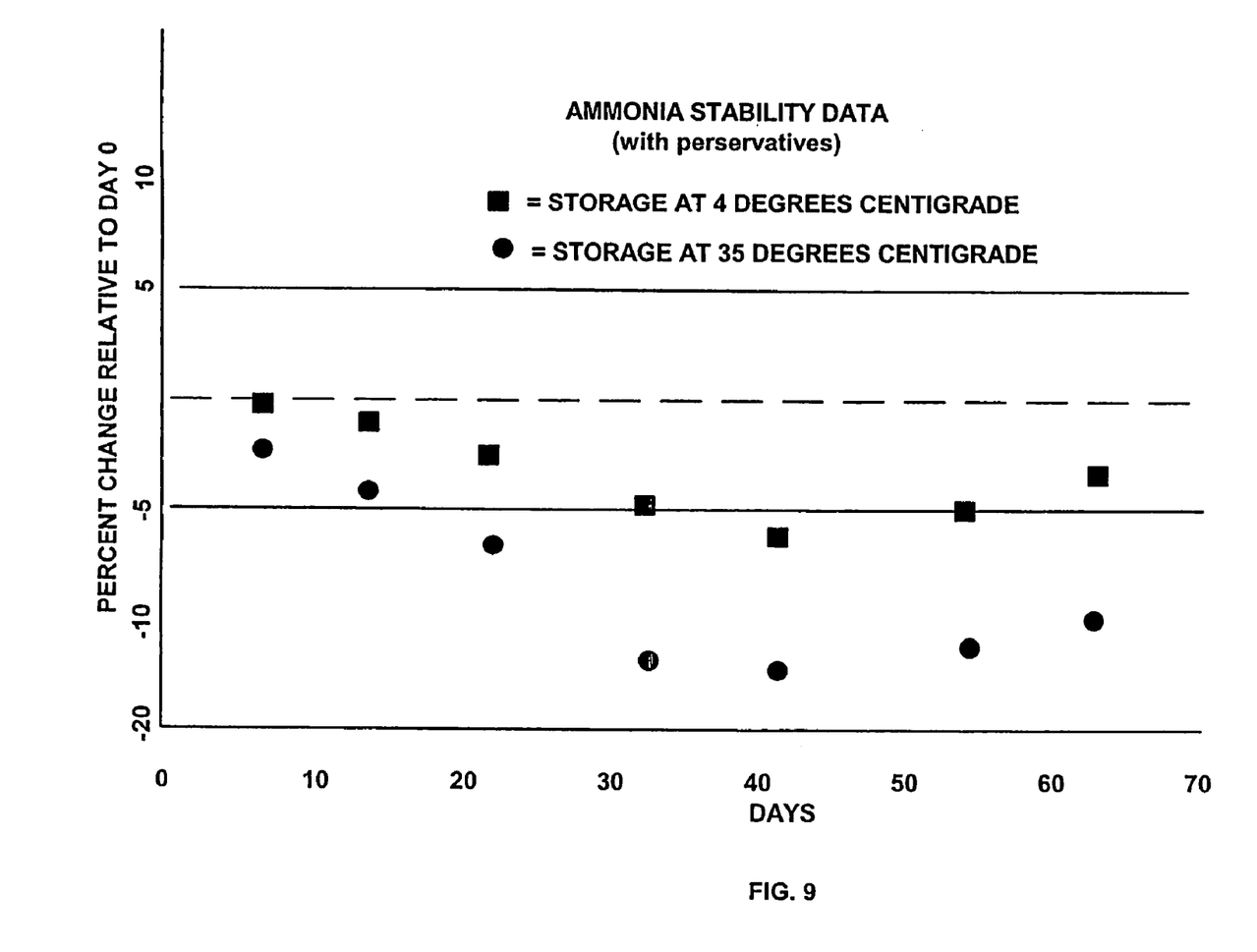
FIG. 9 is an illustration of ammonia stability in an alcohol, carbonate and ammonia multi-analyte calibrator of the present invention with preservatives therein; and, FIG. 9A is an illustration of ammonia stability in an alcohol, carbonate and ammonia multi-analyte calibrator of the present invention without preservatives therein.
Figure 9A:
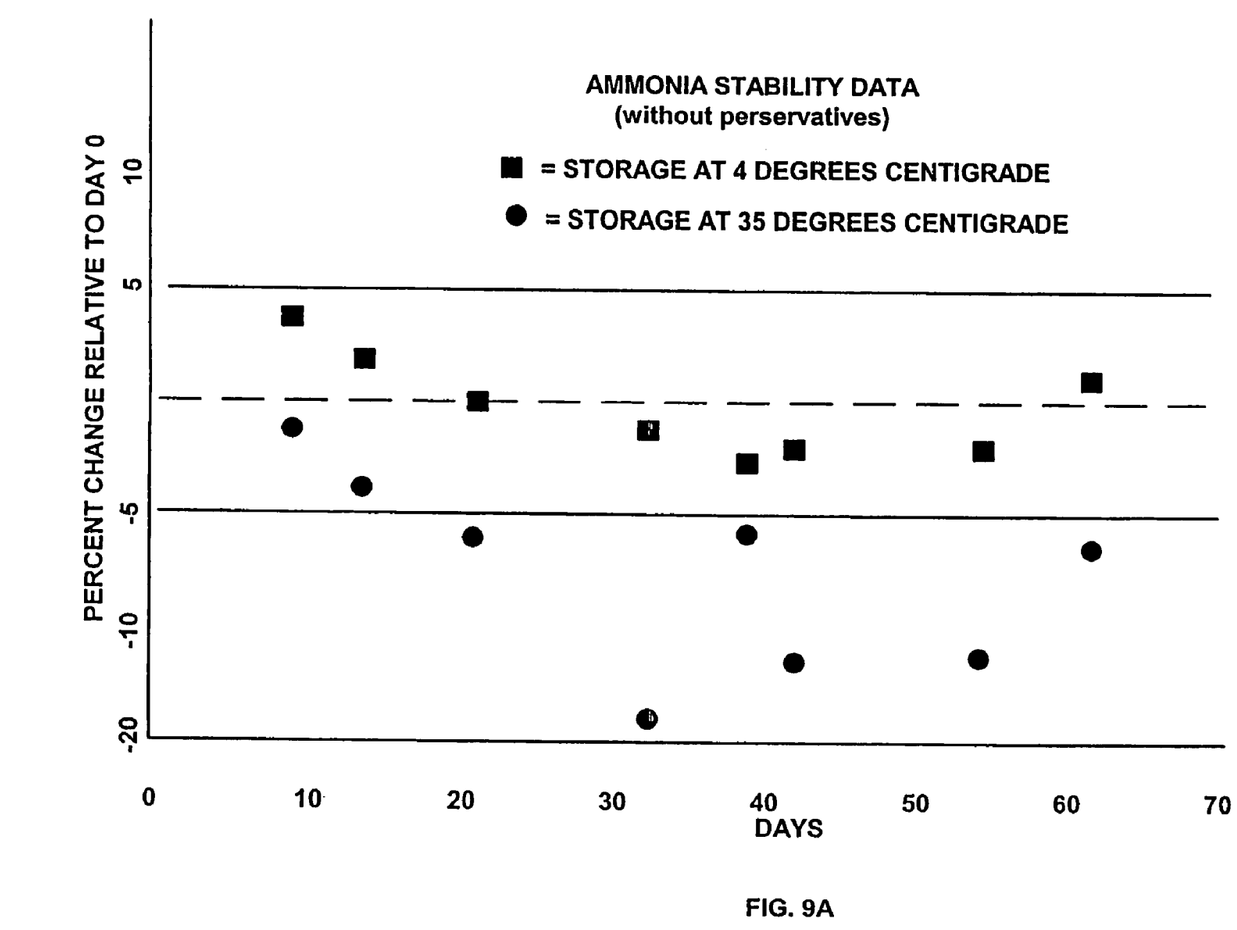

Finally, FIGS. 9 and 9A illustrate ammonia stability as falling outside a ±5% range of a normal 1085 µmol/L value for samples with and without preservatives at about day 15 for a sample stored at +35° C. but remaining generally within the a ±5% range through day 63 stored at 4° C.

This invention will be better understood by reference to the following example which is included here for purposes of exemplification and is not to be considered as limitative. Formulation techniques such as fluid handling, weighing, and mixing are done using standard laboratory equipment (e.g. pipettes, balances, and magnetic stirrers) and techniques known in the industry.

High Level Calibration Solution

Preparation of Three Normal Hydrochloric Acid Solution

Wearing acid gear (face mask, gloves, gauntlets, and rubber apron) and working under a fume hood, place 150 mL of distilled water into a 250 mL volumetric flask. Add 62.5 mL of concentrated HCL. Swirl to mix. Add distilled water to the 250 mL mark. Cap the flask and swirl gently to mix. Transfer to an appropriately sized bottle, cap and label accordingly.

Preparation of High Level Calibration Solution

The following procedure may be employed to provide a "high level" multi-analyte calibration solution having about 5 g/L of Sodium Carbonate, 80 mg/L of Ammonium Bicarbonate, and 3 g/L of Ethyl Alcohol, these levels being about 20% higher than found in normal human serum. Other, mid-range levels of sodium carbonate, ammonium bicarbonate, and ethyl alcohol may be achieved by simply adjusting the initial amounts of analyte added into the calibration solution.

1. Label a 2 L volumetric flask as "AAC Cal High Level" including a lot number, current date and standard safety information. Measure 1500 mL of purified water into the labeled 2 L volumetric flask.

2. Weigh 10.60 g (±0.01 g) of Sodium Carbonate into a plastic beaker. Add the Sodium Carbonate to the labeled 2 L volumetric flask. Rinse beaker with approximately 10 mL of purified water and add to labeled volumetric flask.

3. Weigh 0.166 g (±0.001 g) of Ammonium Bicarbonate into a plastic beaker. Add the Ammonium Bicarbonate to the labeled 2 L volumetric flask. Rinse beaker with approximately 10 mL of purified water and add to labeled volumetric flask.

4. Weigh 6.30 g (±0.01 g) of Ethyl Alcohol into a plastic beaker. Add the Ethyl Alcohol to the labeled 2 L volumetric flask. Rinse beaker with approximately 10 mL of purified water and add to labeled volumetric flask.

5. Add 10.0 mL of Proclin 300 (commercially available from Sigma Aldridge) to the labeled volumetric flask.

6. Add 20 mL of 3N HCL to the labeled volumetric flask.

7. Bring to volume with purified water. Add a magnetic stir bar to the labeled volumetric and mix for 30 minutes at moderate speed.

8. Measure the initial pH reading. Adjust the pH to 8.2 by adding 3N HCL in increments of 2 mL, or less, to the labeled 2 L volumetric flask, mixing after each addition. When results are within acceptable limits pH between 8.0 and 8.4, filter the High Level Calibrator through a 0.22 µ filter into an autoclaved 2 L plastic capped container.

Preparation of Low (Zero) Level Calibration Solution

1. The following procedure may be employed to provide a "zero level" multi-analyte calibration solution not having any Sodium Carbonate, Ammonium Bicarbonate, and Ethyl Alcohol therein, but useful in establishing a zero-level intercept on a calibration curve.

2. Label a 2 L volumetric flask as "AAC Cal Low Level" including a lot number, current date and standard safety information. Measure 1500 mL of purified water into the labeled 2 L volumetric flask.

3. Add 19.98 mL of 3N HCL to the labeled volumetric flask.

4. Add 10.0 mL of Proclin 300 (commercially available from Sigma Aldridge) to the labeled volumetric flask.

5. Bring to volume with purified water. Add a magnetic stir bar to the labeled volumetric and mix for 30 minutes at moderate speed.

6. Measure the pH reading. When results are within acceptable limits pH between 0.0 and 0.2, filter the Low Level Calibrator through a 0.22 µ filter into an autoclaved 2 L plastic capped container.

Stabilization Measurements

Stabilization of the multi-analyte calibration solution of the present invention having controlled and known amounts of sodium carbonate, ammonium bicarbonate, and ethyl alcohol therein may be determined using any of a number of generally accepted criteria. For purposes of the present invention, acceptable stability is defined herein as the multi-analyte calibration solution levels of sodium carbonate, ammonium bicarbonate, and ethyl alcohol changing less than about 5% when the solution is stored in a capped container maintained at a constant temperature of about 4° C. for 400 days.

Techniques for clinical analysis of the amounts of sodium carbonate, ammonium bicarbonate, and ethyl alcohol within the multi-analyte calibration solution of the present invention are well known in the industry. An analyzer like that described in U.S. Pat. No. 5,985,672 and assigned to the assignee of the present invention and calibration techniques like those described in U.S. Pat. No. 6,277,584 and assigned to the assignee of the present invention are typical of such techniques.

In particular, enzymatic carbonate ($ECO_2$) was measured using a phosphoenolpyruvate carboxylase-malate dehydrogenase coupled enzymatic reaction and a stable analog of the cofactor NADH. The bicarbonate anion reacts with phosphoenolpyruvate in the presence of phosphoenolpyruvate carboxylase (PEPC) and $Mg^{++}$ to form oxaloacetate and inorganic phosphate. The oxaloacetate is reduced to malate by malate dehydrogenase (MDH) with simultaneous oxidation of the reduced form of an analog (aNADH) of the cofactor, NADH. The reduction in absorbance of aNADH is proportional to the total $CO_2$ concentration in the sample and is measured bichromatically at wavelengths of 405 nm (primary) and 700 nm (secondary).

Ammonia was measured using an adaptation of the dehydrogenase (GLDH) enzymatic method of van Anken and Schiphorst, Clin Chim Acta 1974; 56:151-157. The substitution of NADPH for NADH eliminates interferences from other NADH-consuming reactions. Glutamate dehydrogenase (GLDH) catalyzes the condensation of ammonia and a-ketoglutarate with simultaneous oxidation of reduced nicotinamide adenine dinucleotide phosphate (NADPH). The decrease in absorbance at 340 nm, due to the disappearance of NADPH, is directly proportional to the ammonia concentration in the sample and is measured using a bichromatic (340, 383 nm) rate technique.

Ethyl alcohol was measured using a modification of the alcohol dehydrogenase (ADH) enzymatic procedure originally described by Bonnichsen and Lundgren and later presented as a general procedure by Bergmeyer. This method uses tris (hydroxymethyl) aminomethane buffer as an aldehyde trapping agent. Alcohol dehydrogenase (ADH) catalyzes the oxidation of ethanol to acetaldehyde, with the simultaneous reduction of nicotinamide adenine dinucleotide (NAD). An alkaline pH and an aldehyde trapping agent force the reaction to one mole of NADH for each mole of alcohol present. The absorbance due to NADH (and thus the alcohol concentration) is determined using a two-filter (340-383 nm) end-point technique.

The terms and expressions which have been employed are used as terms of description and not of limitation, and there is no intention in the use of such terms and expressions of excluding any equivalents of the features shown and described or portions thereof, it being recognized that various modifications are possible within the scope of the invention. It is thus to be understood that the embodiments of the invention disclosed herein are illustrative of the principles of the invention and that other modifications may be employed which are still within the scope of the invention. Accordingly, the present invention is not limited to those embodiments precisely shown and described in the specification but only by the following claims.

What is claimed is:

1. A calibrator suitable for use in clinical assays for blood alcohol, total serum carbonate, and blood ammonia, consisting essentially of:

an aqueous liquid, a known amount of sodium carbonate, a known amount of ammonium bicarbonate, and a known amount of ethyl alcohol, the solution having a pH in the range of about 7.8 to about 8.6, wherein said calibrator is stable when stored at about +4 degrees C.

2. The calibrator of claim 1, wherein said aqueous solution comprises purified water.

3. The calibrator of claim 1, further comprising a preservative.

4. The calibrator of claim 3, wherein the preservative comprises at least one anti-microbial.

5. The calibrator of claim 4, wherein said at least one anti-microbial comprises an antibiotic.

6. The calibrator of claim 3, wherein said calibrator is stable when stored for at least 100 days.

7. The calibrator of claim 1, wherein said calibrator is stable when stored for at least 30 days.

8. A method for calibrating an analyzer capable of conducting assays for at least one of sodium carbonate, ammonium bicarbonate, and ethyl alcohol, said method comprising:

a) adding to a liquid aqueous solution a known amount of sodium carbonate, a known amount of ammonium bicarbonate, and a known amount of ethyl alcohol to form a calibrator;

b) adjusting the solution to have a pH in the range of about 7.8 to about 8.6;

c) using said analyzer to perform an assay on said calibrator; and, d) creating a calibration curve based on the results of said assay for use as a standard in an assay for said at least one of sodium carbonate, ammonium bicarbonate, and ethyl alcohol in a sample.

* * * * *